United States Patent
Unser (10) Patent No.: US 12,035,919 B2
(45) Date of Patent: Jul. 16, 2024

(54) REAL-TIME MONITORING OF FLUID FLOW WITH FLOW SENSING ELEMENT IN AN ANEURYSM AND ASSOCIATED DEVICES, SYSTEMS, AND METHODS

(71) Applicant: KONINKLIJKE PHILIPS N.V., Eindhoven (NL)

(72) Inventor: John Unser, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 517 days.

(21) Appl. No.: 16/100,667

(22) Filed: Aug. 10, 2018

(65) Prior Publication Data
US 2019/0046212 A1    Feb. 14, 2019

Related U.S. Application Data

(60) Provisional application No. 62/543,640, filed on Aug. 10, 2017.

(51) Int. Cl.
*A61B 17/00* (2006.01)
*A61B 5/02* (2006.01)
(Continued)

(52) U.S. Cl.
CPC .... *A61B 17/12113* (2013.01); *A61B 5/02014* (2013.01); *A61B 5/027* (2013.01);
(Continued)

(58) Field of Classification Search
CPC .......... A61B 17/12113; A61B 5/02014; A61B 5/027; A61B 8/06; A61B 8/12;
(Continued)

(56) References Cited

U.S. PATENT DOCUMENTS

| 2003/0120302 A1* | 6/2003 | Minck, Jr. ......... | A61B 17/1215 606/200 |
| 2003/0125790 A1* | 7/2003 | Fastovsky ........... | A61B 5/0215 606/108 |

(Continued)

FOREIGN PATENT DOCUMENTS

WO    WO-2017074411 A1 *    5/2017    ........... A61L 31/022

OTHER PUBLICATIONS

Pedersen, Nicholas et al, "A MEMS-Based Vortex Flow Sensor for Aggressive Media", (2003), Proceedings of IEEE Sensors 2003 (IEEE Cat. No. 03CH37498) 1 p. 320-325.

(Continued)

*Primary Examiner* — Shahdeep Mohammed
*Assistant Examiner* — Adam D. Kolkin (57) ABSTRACT

Embodiments of the present disclosure are configured to assess effectiveness of an endovascular aneurysm coiling procedure. A system is provided that can include a flow sensing element supported by a structure that can position and retain the sensing element within the aneurysm. A computer in communication with the sensing element can detect a measurement of fluid flow entering the aneurysm based on data obtained by the sensing element after positioning the structure and element within an aneurysm. A wire segment can pass through the elongate member and form a coil in the aneurysm as the wire segment is passed through the elongate member. The sensing element can provide fluid flow measurements from within the aneurysm after the elongate member is removed from the vasculature.

20 Claims, 6 Drawing Sheets

(51) Int. Cl.
- *A61B 5/027* (2006.01)
- *A61B 8/00* (2006.01)
- *A61B 8/06* (2006.01)
- *A61B 8/12* (2006.01)
- *A61B 17/12* (2006.01)
- *A61B 8/08* (2006.01)

(52) U.S. Cl.
CPC ............... *A61B 8/06* (2013.01); *A61B 8/12* (2013.01); *A61B 8/56* (2013.01); *A61B 17/1214* (2013.01); *A61B 8/0808* (2013.01); *A61B 8/4483* (2013.01); *A61B 2017/00022* (2013.01); *A61B 2017/1205* (2013.01)

(58) Field of Classification Search
CPC ....... A61B 8/56; A61B 7/1214; A61B 8/0808; A61B 8/4483; A61B 2017/00022; A61B 2017/1205
See application file for complete search history.

(56) References Cited

U.S. PATENT DOCUMENTS

| | | | | |
|---|---|---|---|---|
| 2004/0267115 | A1* | 12/2004 | Carr | A61B 5/027 600/433 |
| 2007/0141099 | A1* | 6/2007 | Buiser | A61B 17/1215 427/2.26 |
| 2007/0288050 | A1* | 12/2007 | Davis | A61B 17/1219 606/191 |
| 2008/0243168 | A1* | 10/2008 | Ho | A61M 25/1011 606/194 |
| 2010/0069757 | A1* | 3/2010 | Yoshikawa | A61B 5/02007 600/454 |
| 2016/0022222 | A1* | 1/2016 | Folk | A61B 6/504 600/481 |
| 2017/0224355 | A1* | 8/2017 | Bowman | B21F 3/04 |
| 2017/0367579 | A1* | 12/2017 | Reiner | G16H 40/63 |
| 2018/0168732 | A1* | 6/2018 | Trousset | A61B 6/5211 |
| 2018/0193026 | A1* | 7/2018 | Yang | A61F 2/90 |

OTHER PUBLICATIONS

Van Der Horst, Arjen et al "A Novel Flexible Thermoelectric Sensor for Intravascular Flow Assessment," (2013), JSEN_IEEE Sensors Journal (JSEN) XX (XX) p. 1-1.

Takahata, Kenichi et al "A Wireless Microsensor for Monitoring Flow and Pressure in a Blood Vessel Utilizing a Dual-Inductor Antenna Stent and Two Pressure Sensors," (2004), MEMS_IEEE International Conference on Micro Electro Mechanical Systems (MEMS) p. 216-219.

Saito, Yasuhiro et al "Assessment of Coronary Flow Reserve with Fast Cine Phase Contrast Magnetic Resonance Imaging: Comparison With Measurement by Doppler Guide Wire," 1999, JMRI_Journal of Magnetic Resonance Imaging (JMRI) 10 (4) p. 563-568.

Font, Davinia et al "Characterization of a Low-Cost Optical Flow Sensor When Using an External Laser as a Direct Illumination Source," 2011, Sensors 11 (12) p. 11856-70.

Marana, Michael A. Development of a Bio-Inspired Magnetostrictive Flow and Tactile Sensor, 2012.

* cited by examiner

REAL-TIME MONITORING OF FLUID FLOW WITH FLOW SENSING ELEMENT IN AN ANEURYSM AND ASSOCIATED DEVICES, SYSTEMS, AND METHODS

TECHNICAL FIELD

The present disclosure relates generally to the improvements in treating aneurysms in a vessel of a vasculature. Aspects of the present disclosure are particularly suited for monitoring the effectiveness of an endovascular aneurysm coiling procedure. For example, some particular embodiments of the present disclosure are specifically configured for monitoring fluid flow into the aneurysm during and after the coiling procedure.

BACKGROUND

One accepted treatment of a vessel aneurysm, such as those in the brain, is "open surgical clipping" which is performed by a neurosurgeon who makes an incision in the skin over the head, makes an opening in the bone, and dissects through spaces of the brain to place a clip across the aneurysm where it arises from the blood vessel. This prevents the blood flow from entering the aneurysm. Most elective patients spend 2-3 nights in the hospital and then will go home on light restricted activity for 1-2 months after surgery. Many neurosurgeons can perform mini craniotomies, or eye brow incisions to clip an aneurysm. In select patients a small incision is made over the eyebrow. A small two inch window is then made in the bone over the eye and through this incision a small clip is placed across the opening of the aneurysm. These patients usually spend 1-2 days in the hospital after surgery and then go home. Patients are usually on light restricted activity for 1-2 months after surgery. However, this is still an invasive procedure and takes longer to recover from than a coiling procedure.

Another accepted treatment of a vessel aneurysm is a coiling procedure. A coiling procedure is performed as an extension of the angiogram. A catheter is inserted into a vessel over the hip and other catheters are navigated through the blood vessels to the vessels of the brain and into the aneurysm. Coils are then packed into the aneurysm up to the point where it arises from the blood vessel, preventing blood flow from entering the aneurysm. Most elective patients will go home the next day after surgery and are back to normal activities the following day.

Aneurysmal subarachnoid hemorrhage (aSAH) is a disastrous and potentially fatal medical emergency requiring immediate intervention as approximately 12% of patients die before receiving medical supports, and approximately 50% of survivors suffer from permanent disability and dependency. Endovascular coiling has increasingly become an alternative procedure for surgical clipping in both ruptured and unruptured aneurysms. However, there are considerable risks and complications such as thromboembolism, aneurysm rupture, patent artery occlusion, coil migration and vasospasm in endovascular therapy. Despite the advancements in coiling 1 out of 10 patients will undergo a second procedure to place more coils in the aneurysm to stem the flow of blood into the aneurysm.

Accordingly, there remains a need for improved devices, systems, and methods for assessing the effectiveness of the coiling procedure to prevent fluid flow into the aneurysm.

SUMMARY

Embodiments of the present disclosure are configured to measure fluid flow entering an aneurysm utilizing a flow sensing element positioned within the aneurysm. In some embodiments, the flow sensing element can be attached to structure that is passed into the aneurysm through a catheter. For example, the structure may be wire segment used to fill the aneurysm during an endovascular coiling procedure. The flow sensing element can be left within the aneurysm to allow flow detection during and after the procedure. For example, the flow sensing element can be a radio frequency (RF) device in communication with an RF transceiver. Advantageously, the flow sensing element can monitor flow after the patient is done with the procedure because the flow sensing element is left inside of the aneurysm.

Embodiments of the present disclosure are configured to measure fluid flow entering an aneurysm utilizing an intravascular device having a flow-sensing element mounted within a distal portion of an intravascular device.

In some instances, a system is provided that can include a structure configured to pass through a vasculature and a flow sensing element supported by the structure can be included, where the structure is positioned in an aneurysm and retains the flow sensing element within the aneurysm. A computer in communication with the flow sensing element can be configured to detect, after the structure is being positioned within an aneurysm, a measurement of fluid flow entering the aneurysm based on data obtained by the flow sensing element.

In some instances, a method of evaluating an endovascular aneurysm coiling procedure is provided, where the method can include operations of detecting, at a computer and after positioning a coil within an aneurysm of a vessel in a vasculature, a first measurement of fluid flow entering the aneurysm based on data obtained by a flow sensing element disposed in the aneurysm, with the flow sensing element in communication with a computer, determining, at the computer, that the first fluid flow measurement is at or below an acceptable level, and outputting, to a display in communication with the computer, a first graphical representation that the first fluid flow measurement is at or below the acceptable level.

Other devices, systems, and methods specifically configured to interface with such devices and/or implement such methods are also provided.

Additional aspects, features, and advantages of the present disclosure will become apparent from the following detailed description along with the drawings.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or operations described with respect to one embodiment may be combined with the features, components, and/or operations described with respect to other embodiments of the present disclosure. For the sake of brevity, however, the numerous iterations of these combinations will not be described separately.

The disclosure may repeat reference numerals and/or letters in the various examples or Figures. This repetition is for the purpose of simplicity and clarity and does not in itself dictate a relationship between the various embodiments and/or configurations discussed. Further, spatially relative terms, such as beneath, below, lower, above, upper, and the like, may be used herein for ease of description to describe one element or feature's relationship to another element(s) or feature(s) as illustrated, the upward direction being toward the top of the corresponding figure and the downward direction being toward the bottom of the corresponding figure. Unless otherwise stated, the spatially relative terms are intended to encompass different orientations of the apparatus in use or operation in addition to the orientation depicted in the Figures. For example, if an apparatus in the Figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

As used herein, the words "comprise," "have," "include," and all grammatical variations thereof are each intended to have an open, non-limiting meaning that does not exclude additional elements or operations. While compositions and methods are described in terms of "comprising," "containing," or "including" various components or operations, the compositions and methods also can "consist essentially of" or "consist of" the various components and operations. It should also be understood that, as used herein, "first," "second," and "third," are assigned arbitrarily and are merely intended to differentiate between two or more objects, etc., as the case may be, and does not indicate any sequence. Furthermore, it is to be understood that the mere use of the word "first" does not require that there be any "second," and the mere use of the word "second" does not require that there be any "first" or "third," etc.

The terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

Figure 1:
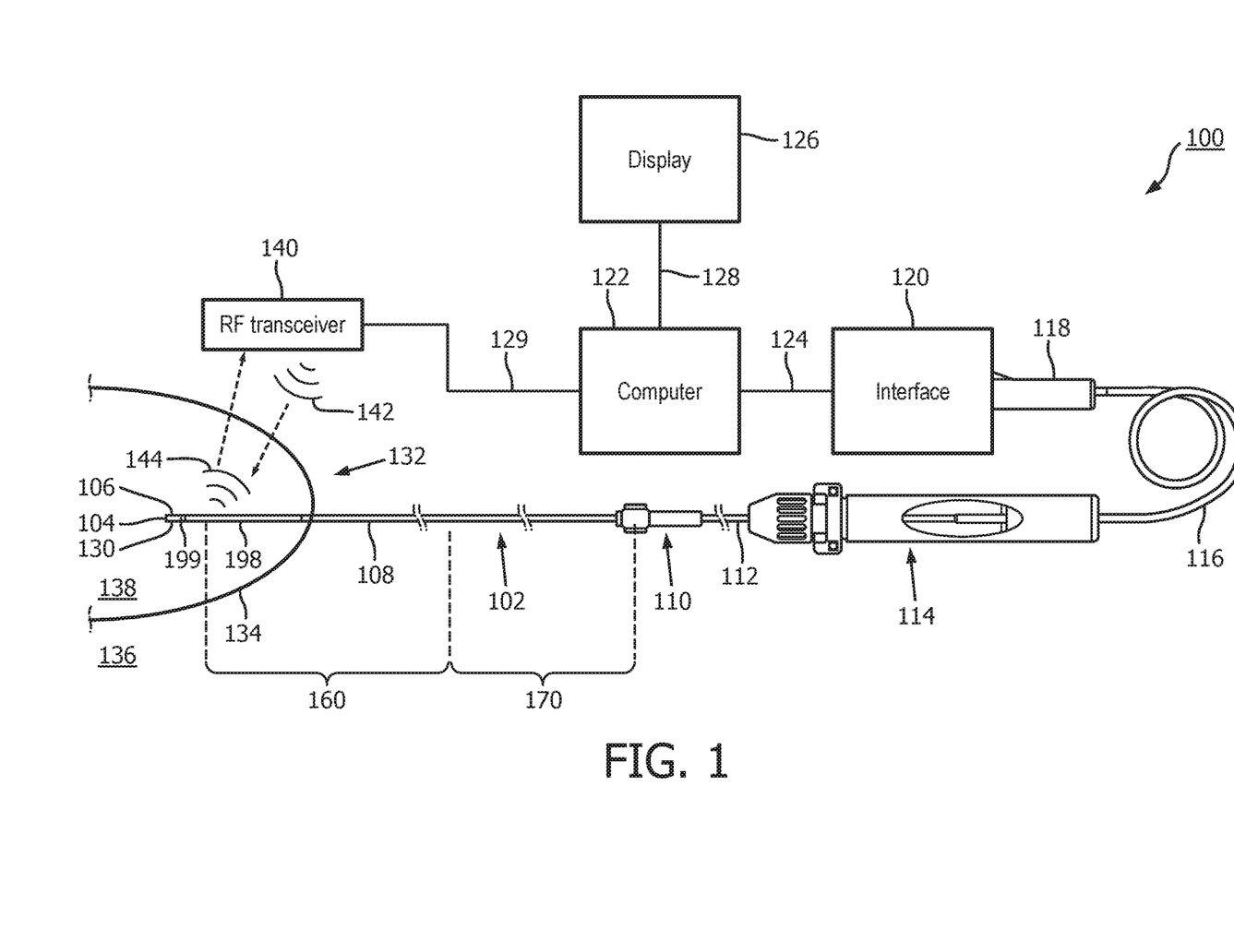
FIG. 1 is a diagrammatic, schematic view of a system according to an embodiment of the present disclosure that can perform an endovascular aneurysm coiling procedure.

Referring to FIG. 1, shown therein is a system 100 according to an embodiment of the present disclosure. The system 100 can include an instrument 102, that can be any form of device, instrument, or probe sized and shaped to be positioned within a vessel. The vessel 200 can be positioned within an internal region 138 of a patient's body. The internal region 138 is separated from the external region 136 the skin 134 of the patient. In the illustrated embodiment, instrument 102 is generally representative of a guide wire. In other embodiments, instrument 102 may be a catheter, including a rapid-exchange catheter or an over-the-wire catheter. The instrument 102 can also include a micro-catheter that may be inserted through a lumen in a guide catheter that has been previously inserted into the vessel. The micro-catheter can be used to extend into smaller vessels in a vasculature. The micro-catheter can also include a lumen therethrough for guiding objects and/or sensors to desired locations in the vasculature.

The instrument 102 can include a distal portion 160 and proximal portion 170. The instrument 102 can be configured to obtain diagnostic information about a vessel 200 (see FIG. 2) in which the instrument is positioned and/or information about additional structures adjacent the vessel 200. In that regard, the instrument 102, at the distal portion 160, can include one or more sensors 130, transducers 130, and/or other monitoring elements 130 configured to obtain the diagnostic information. The diagnostic information can include one or more of flow (velocity), flow (volume), pressure, images (including images obtained using ultrasound (e.g., IVUS), OCT, thermal, and/or other imaging techniques), temperature, and/or combinations thereof. The one or more sensors, transducers, and/or other monitoring elements 130 are positioned adjacent a distal portion 160 of the instrument 102 in some instances. In that regard, the one or more sensors, transducers, and/or other monitoring elements 130 are positioned less than 30 cm, less than 10 cm, less than 5 cm, less than 3 cm, less than 2 cm, and/or less than 1 cm from a distal tip 104 of the instrument 102 in some instances. In some instances, at least one of the one or more sensors, transducers, and/or other monitoring elements 130 is positioned at the distal tip 104 of the instrument 102.

Figure 2:
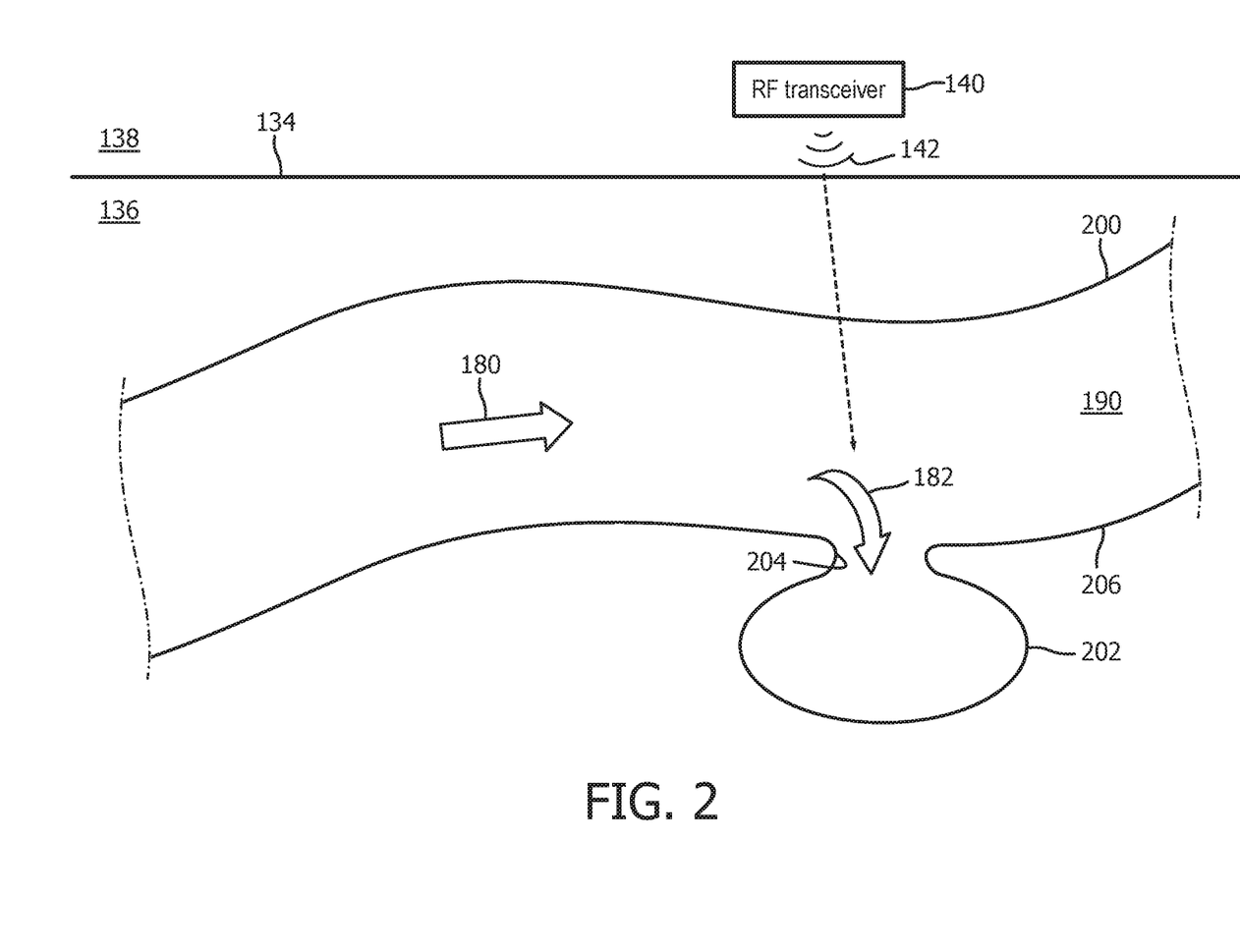
FIG. 2 is a diagrammatic, partial cross-sectional view of an aneurysm in a wall of a vessel in a vasculature.

The instrument 102 includes at least one flow sensing element 130 configured to monitor flow within a vessel 200, which can include other structures such an aneurysm 202 in a wall 206 of the vessel 200 (see FIG. 2). The flow sensing element (or flow monitoring) element 130 can take on the form of a radio frequency (RF) transducer 130. The RF transducer 130 can detect fluid flow in a channel and wirelessly transmit flow measurements to an RF transceiver 140. The RF transducer 130 can be powered by electromagnetic signals generated by the RF transceiver 140 and wirelessly transmitted to the RF transducer 130. The powered RF transducer 130 can detect fluid flow and transmit the data to the RF transceiver 140 via electromagnetic signals. The flow sensing (or flow monitoring) element 130 can take the form of an ultrasound transducer 130. For example, in some instances the flow sensing element 130 is an ultrasound transducer 130 configured to detect Doppler shifts in blood flow. In some instances, the flow sensing element 130 includes a vortex flow sensor as described in "A MEMS-Based Vortex Flow Sensor for Aggressive Media," Nicholas Pedersen, Per E Andersen (2003), *Proceedings of IEEE Sensors* 2003 *(IEEE Cat. No. 03CH37498)* 1 p. 320-325, which is hereby incorporated by reference in its entirety. In some instances, the flow sensing element 130 includes a thermoelectric (thermodilution) flow sensor as described in "A Novel Flexible Thermoelectric Sensor for Intravascular Flow Assessment," Arjen van der Horst, Dennis van der Voort, Benjamin Mimoun, Marcel C M Rutten, Frans N van de Vosse, Ronald Dekker (2013), *JSEN_IEEE Sensors Journal (JSEN)* XX (XX) p. 1-1, which is hereby incorporated by reference in its entirety.

In some instances, the flow sensing element 130 includes a sensor as described in "A Wireless Microsensor for Monitoring Flow and Pressure in a Blood Vessel Utilizing a Dual-Inductor Antenna Stent and Two Pressure Sensors," Kenichi Takahata, Andrew D DeHennis, Kensall D Wise, Yogesh B Gianchandani (2004), *MEMS_IEEE International Conference on Micro Electro Mechanical Systems (MEMS)* p. 216-219, which is hereby incorporated by reference in its entirety. In some instances, magnetic resonance imaging (MRI) is utilized to monitor flow within the vessel as described in "Assessment of Coronary Flow Reserve with Fast Cine Phase Contrast Magnetic Resonance Imaging: Comparison With Measurement by Doppler Guide Wire," M Shibata, H Sakuma, N Isaka, K Takeda, C B Higgins, T Nakano (1999), *JMRI_Journal of Magnetic Resonance Imaging (JMRI)* 10 (4) p. 563-568, which is hereby incorporated by reference in its entirety. In some instances, the flow sensing element 130 includes an optical flow sensor, such as those described in "Characterization of a Low-Cost Optical Flow Sensor When Using an External Laser as a Direct Illumination Source," Davinia Font, Marcel Tresanchez, Tomas Palleja, Merce Teixido, Jordi Palacin (2011), *Sensors* 11 (12) p. 11856-70, which is hereby incorporated by reference in its entirety. In some instances, the flow sensing element 130 includes a magnetostrictive sensor, such as those described in "Development of a Bio-Inspired Magnetostrictive Flow and Tactile Sensor, Michael Adam Marana (2012), which is hereby incorporated by reference in its entirety.

In some instances, the instrument 102 includes at least one pressure monitoring element in addition to the flow sensing element 130. In that regard, the pressure monitoring element can be a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. An example of a commercially available guide wire product that includes both flow and pressure monitoring elements is the ComboWire® XT pressure and flow guide wire available from Volcano Corporation. Generally, the instrument 102 is sized such that it can be positioned through a vessel without significantly impacting fluid flow through the vessel that could impact the flow readings. Accordingly, in some instances the instrument 102 has an outer diameter of 0.018" or less. In some embodiments, the instrument 102 has an outer diameter of 0.014" or less.

In the illustrated embodiment, the instrument 102 is a catheter (e.g. a micro catheter) having a distal tip 104 and a housing 106 positioned adjacent the distal tip. The housing 106 is configured to house one or more sensors, transducers, and/or other monitoring elements configured to obtain the diagnostic information about the vessel. In the illustrated embodiment, the housing 106 contains at least a flow sensor configured to monitor a flow within a lumen (such as a vessel) in which the instrument 102 is positioned. A shaft 108 extends proximally from the housing 106. A torque device 110 is positioned over and coupled to a proximal portion 170 of the shaft 108. A proximal end portion 112 of the instrument 102 is coupled to a connector 114. A cable 116 extends from connector 114 to a connector 118. In some instances, connector 118 is configured to be plugged into an interface 120. In that regard, interface 120 is a patient interface module (PIM) in some instances. In some instances, the cable 116 is replaced with a wireless connection. In that regard, it is understood that various communication pathways between the instrument 102 and the interface 120 may be utilized, including physical connections (including electrical, optical, and/or fluid connections), wireless connections, and/or combinations thereof.

The interface 120 is communicatively coupled to a computer 122 via a connection 124. As used herein, "computer" can include any device suitable for performing the processing and analysis techniques discussed within the present disclosure. Therefore, "computer" can include computing devices, desktop computers, laptops, tablets, smartphones, microprocessors, reduced instruction set controllers (RISCs), field programmable gate arrays (FPGAs), application specific integrated circuits (ASICs), etc. In some embodiments, the computer 122 includes a processor, random access memory, and a storage medium. In that regard, in some particular instances the computer 122 is programmed to execute operations associated with the data acquisition and analysis described herein. Accordingly, it is understood that any operations related to data acquisition, data processing, instrument control, and/or other processing or control aspects of the present disclosure may be implemented by the computer using corresponding instructions stored on or in a non-transitory computer readable medium accessible by the computer. In some instances, the computer 122 is a console device. In some particular instances, the computer 122 is similar to the s5™ Imaging System or the s5i™ Imaging System, each available from Volcano Corporation. In some instances, the computer 122 is portable (e.g., handheld, on a rolling cart, etc.). Further, it is understood that in some instances the computer 122 comprises a plurality of computers. In that regard, it is particularly understood that the different processing and/or control aspects of the present disclosure may be implemented separately or within predefined groupings using a plurality of computers. Any divisions and/or combinations of the processing and/or control aspects described below across multiple computers are within the scope of the present disclosure.

Together, connector 114, cable 116, connector 118, interface 120, and connection 124 facilitate communication between the one or more sensors, transducers, and/or other monitoring elements of the instrument 102 and the computer 122. However, this communication pathway is exemplary in nature and should not be considered limiting in any way. In that regard, it is understood that any communication pathway between the instrument 102 and the computer 122 may be utilized, including physical connections (including electrical, optical, and/or fluid connections), wireless connections, and/or combinations thereof. In that regard, it is understood that the connection 124 is wireless in some instances. In some instances, the connection 124 includes a communication link over a network (e.g., intranet, internet, telecommunications network, and/or other network). In that regard, it is understood that the computer 122 can be positioned remote from an operating area where the instrument 102 is being used in some instances. Having the connection 124 include a connection over a network can facilitate communication between the instrument 102 and a remote computer 122 regardless of whether the computer is in an adjacent room, an adjacent building, or in a different state/country. Further, it is understood that the communication pathway between the instrument 102 and the computer 122 is a secure connection in some instances. Further still, it is understood that, in some instances, the data communicated over one or more portions of the communication pathway between the instrument 102 and the computer 122 is encrypted.

The display 126 is communicatively coupled to the computer 122 via a connection 128. Similar to the connection 124 between interface 120 and the computer 122, it is understood that any communication pathway between the display 126 and the computer 122 may be utilized, including physical connections (including electrical, optical, and/or fluid connections), wireless connections, and/or combinations thereof. In that regard, it is understood that the connection 128 is wireless in some instances. In some instances, the connection 128 includes a communication link over a network (e.g., intranet, internet, telecommunications network, and/or other network). In that regard, it is understood that the computer 122 is positioned remote from the display 126 in some instances. Having the connection 128 include a connection over a network can facilitate communication between the display 126 and the remote computer 122 regardless of whether the computer is in an adjacent room, an adjacent building, or in a different state/country.

An RF transceiver 140 is communicatively coupled to the computer 122 via a connection 129. Similar to the connection 124 between interface 120 and the computer 122, it is understood that any communication pathway between the RF transceiver 140 and the computer 122 may be utilized, including physical connections (including electrical, optical, and/or fluid connections), wireless connections, and/or combinations thereof. In that regard, it is understood that the connection 129 is wireless in some instances. In some instances, the connection 129 includes a communication link over a network (e.g., intranet, internet, telecommunications network, and/or other network). In that regard, it is understood that the computer 122 is positioned remote from the RF transceiver 140 in some instances. Having the connection 129 include a connection over a network can facilitate communication between the RF transceiver 140 and the remote computer 122 regardless of whether the computer is in an adjacent room, an adjacent building, or in a different state/country.

The RF transceiver 140 can transmit electromagnetic signals 142 from an external region 136 to an RF transducer 130 that can be positioned at a distal tip 104 in an internal region 138. The RF transducer 130 can receive the energy supplied by the electromagnetic signals 142 to power the RF transducer 130, make flow measurements of fluid flowing in a lumen in the internal region 138, and transmit electromagnetic signals 144 from the internal region 138, through the skin 134 and to the RF transceiver 140. The RF transceiver 140 can receive the electromagnetic signals 144 from the RF transducer 130, which can contain data that is representative of the fluid flow in the lumen, and transfer the received data to the computer 122 for processing.

The instrument 102 can include a first flexible elongate member (such as a guide catheter 198 with a distal end 199), with a second flexible elongate member (such as microcatheter 194 with the distal tip 104 and the housing 106). The flow sensing element 130 can be positioned in an aneurysm 202 that is proximate the distal tip 104. The flow sensing element 130 can be an RF transducer that can transmit flow sensor data to the RF transceiver via electromagnetic signals 144.

It is understood that one or more components of the system 100 are not included, are implemented in a different arrangement/order, and/or are replaced with an alternative device/mechanism in other embodiments of the present disclosure. For example, in some instances, the system 100 does not include interface 120. In such instances, the connector 118 (or other similar connector in communication with instrument 102) may plug into a port associated with computer 122. Alternatively, the instrument 102 may communicate wirelessly with the computer 122. Generally speaking, the communication pathway between the instruments 102 and the computer 122 may have no intermediate nodes (i.e., a direct connection), one intermediate node between the instrument and the computer, or a plurality of intermediate nodes between the instrument and the computer.

Referring to FIG. 2, shown therein is an enlarged representative partial cross-sectional view of a vessel 200 of an intravascular system of a patient undergoing a catheterization procedure to treat an aneurysm. As shown, the aneurysm 202 has formed in the wall of the vessel 200. Without treatment, this aneurysm 202 could burst causing the patient to hemorrhage through the opening 204 in the wall 206 of the vessel 200. As stated above, the RF transceiver 140 can transmit electromagnetic signals 142 from an external region 136, through the skin 134, and into the internal region 138.

Endovascular coiling has increasingly become an alternative procedure for surgical clipping in both ruptured and unruptured aneurysms. However, there are considerable risks and complications such as thromboembolism, aneurysm rupture, patent artery occlusion, coil migration and vasospasm in endovascular therapy. Despite the advancements in coiling 1 out of 10 patients will undergo a second procedure to place more coils in the aneurysm 202 to stem the flow 182 of blood into the aneurysm 202. By measuring the effectiveness of coiling during the procedure can significantly reduce the number of patients that have to undergo a second procedure and its associated risks. Coiling involves approaching the aneurysm 202 through an internal flow passage 190 of the vessel 200, avoiding the need to open the patient's skull. Small metal coils can be inserted into and/or formed in the aneurysm 202. The coils remain in the aneurysm 202 after the procedure. They prevent blood from flowing into the aneurysm and therefore reduce the risk of a bleed or a re-bleed. Blood then clots in and around the coils sealing off the weakened area.

Figure 3:
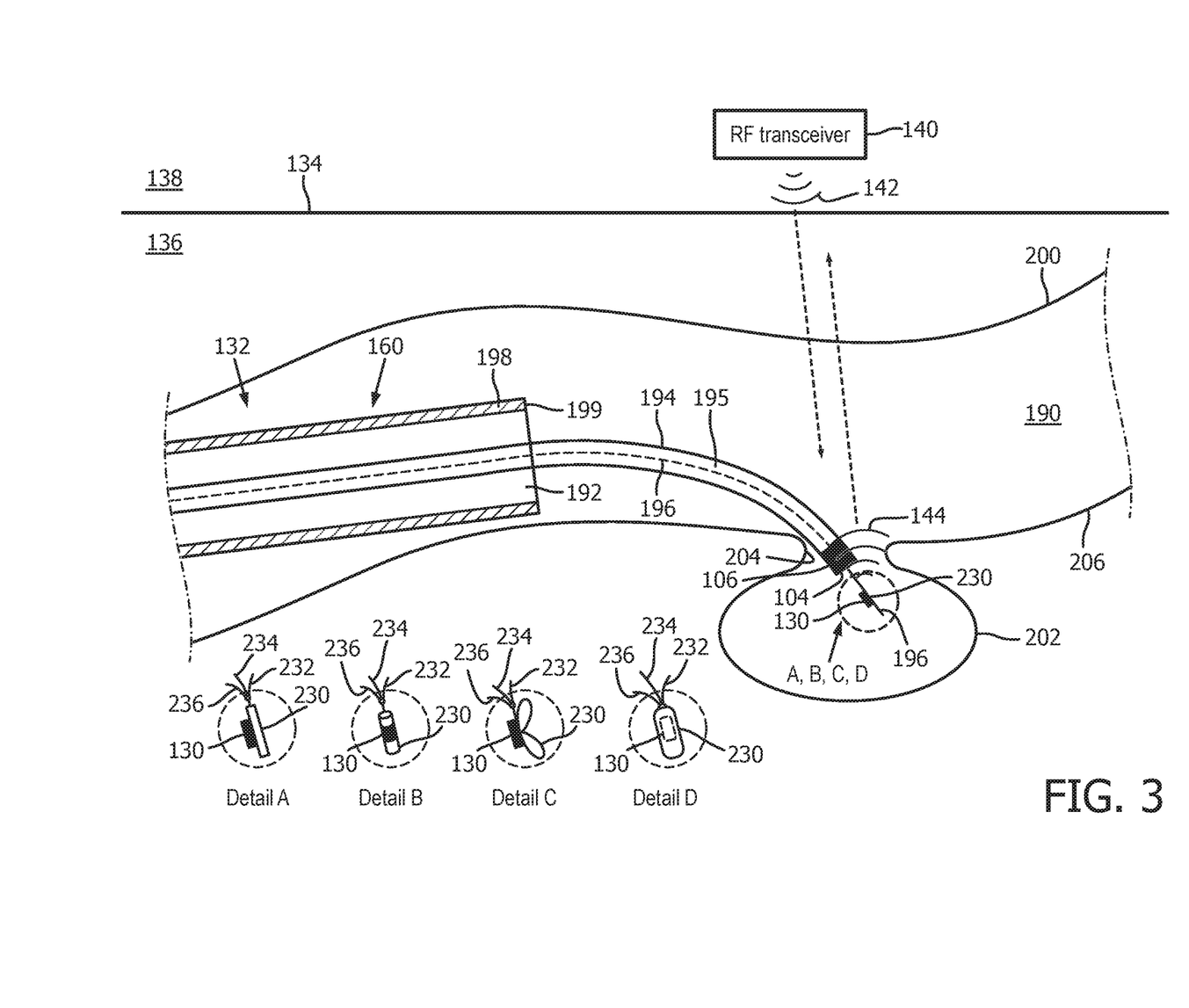
FIG. 3 is a diagrammatic, partial cross-sectional view of the vessel of FIG. 2 with a distal portion of a catheterization instrument installed proximate the aneurysm, with a distal tip of a micro-catheter positioned within the aneurysm, and a flow sensing element positioned within the aneurysm, with various structures securing the flow sensing element in the aneurysm.

Referring to FIG. 3, shown therein is an enlarged representative partial cross-sectional view a catheter system extended through the flow passage 190 of the vessel 200. Initially, a guidewire (not shown) can be inserted into the body of the patient and extended through the vasculature to a position proximate the aneurysm 202. Once the guidewire is properly positioned, a guide catheter 198 with a distal end 199 and a lumen 192 with a central longitudinal axis extending therethrough, can be slid along the guidewire until the distal end 199 of the guide catheter 198 is properly positioned in the vessel 200 proximate the aneurysm 202. The guidewire can then be removed from the lumen 192 of the guide catheter 198 to allow insertion of a micro-catheter 194.

The micro-catheter 194 can also include a lumen 195 with a central longitudinal axis extending therethrough to allow passage of coils 210 and/or passage of a wire segment 196 that can form a coil 210 in the aneurysm 202. The micro-catheter 194 can be extended through the guide catheter 198 until the distal tip 104 extends from the distal end 199 of the guide catheter 198. The distal tip 104 can be steered through the opening 204 and extend into the aneurysm 202. The flow sensing element 130 (e.g. an RF transducer) can be configured to detect fluid (e.g. blood) flow 182 entering the aneurysm 202. FIG. 3 indicates that the flow sensing element 130 is attached to the wire segment 196. Therefore, when the wire segment 196 is pushed into the aneurysm 202, it forms a coil 210 and the flow sensing element 130 remains in the aneurysm 202 with the coil 210. However, the flow sensing element 130 can be mounted or secured by any suitable structure 230, such as the wire segment 196, as long as the flow sensing element 130 can detect fluid flow 182 entering the aneurysm 202.

It should be understood, that this procedure can also be performed without using a guidewire, or guide catheter 198. The micro-catheter 194 can be inserted into the vasculature and maneuvered such that the distal tip 104 extends into the aneurysm. Then the wire segments 196 can be passed through the lumen 195 into the aneurysm 202 to form the coil(s) 210.

Detail views A, B, C, D of FIG. 3 illustrate additional examples of the flow sensing element 130 mounted to suitable structures 230 to form an assembly 238. Each detail view A, B, C, D represent alternatives to the configuration shown in FIG. 3. Each detail view A, B, C, D shows a distal end 236 of a flexible elongate member 234 releasably attached to the structure 230 via detachable connector 232. When the assembly 238 is positioned in the aneurysm 202, then the detachable connector 232 can be detached thereby releasing the assembly 238 from the distal end 236 and depositing the assembly 238 into the aneurysm 202. The structure 230 can be shaped to improve retention of the flow sensing element 130 in the aneurysm 202.

Detail view A shows the flow sensing element 130 attached to a structure 230 that is in the form of a substrate, the substrate can be various thicknesses as well as various shapes. For example, the substrate can be round, square, oval, triangular, rectangular, polygonal, etc. with a uniform thickness or varied thickness across the shape. The flow sensing element 130 can be secured to the structure 230 by fixedly attaching the element 130 to the structure 230 by various means, such as with an adhesive. A protective film or coating can be formed over the flow sensing element 130 to encapsulate the flow sensing element 130 on the structure 230. However, it is not required that the flow sensing element 130 or assembly 238 be encapsulated. Also, any coating of film may not interfere with reception and transmission of electromagnetic signals.

Detail view B shows a cylindrical structure 230 with the flow sensing element 130 disposed between two opposite ends of the cylindrical structure 230. Again, a surface coating or film can be used to encapsulate the assembly 238.

Detail view C shows a flexible structure 230 attached to the flow sensing element 130. The flexible structure 230 can be made from a flexible material, such as a ribbon of plastic, a flexible wire segment, and a flexible thread (such as waxed textile thread, dental floss material, etc.).

Detail view D shows a container structure 230 that can be used to contain the flow sensing element 130 within an internal volume of the container structure 230. The container structure 230 can be any suitable container that can house the flow sensing element 130 within an internal volume (such as a capsule, a coating applied to the flow sensing element 130 to form the structure 230, a film wrapped around the flow sensing element 130 etc.) and not interfere with reception and transmission of electromagnetic signals.

The RF transceiver 140 can transmit electromagnetic signals 142 from the external region 136, through skin 134, through at least a portion of the internal region 138, and radiate the RF transducer 130 that has been positioned in the aneurysm 202. The electromagnetic signals 142 can induce electrical power in the RF transducer 130, providing power for onboard circuitry that can detect fluid flow entering aneurysm 202. The onboard circuitry can transmit electromagnetic signals 144 from the aneurysm 202, through the internal region 138, back through the skin 134 and through a portion of the external region 136 to the RF transceiver 140. The RF transceiver 140, can interpret the received electromagnetic signals 144, or merely condition them for transmission to the computer 122, which can interpret them. The electromagnetic signals 144 can continue to be generated even after the guide catheter 198 and micro-catheter 194 are removed from the patient.

It should be understood that it is not a requirement that the electromagnetic signals 142 induce power in the RF transducer 130. Batteries can be used to supply power to the onboard circuits, as well as other power supply techniques.

Figure 4:
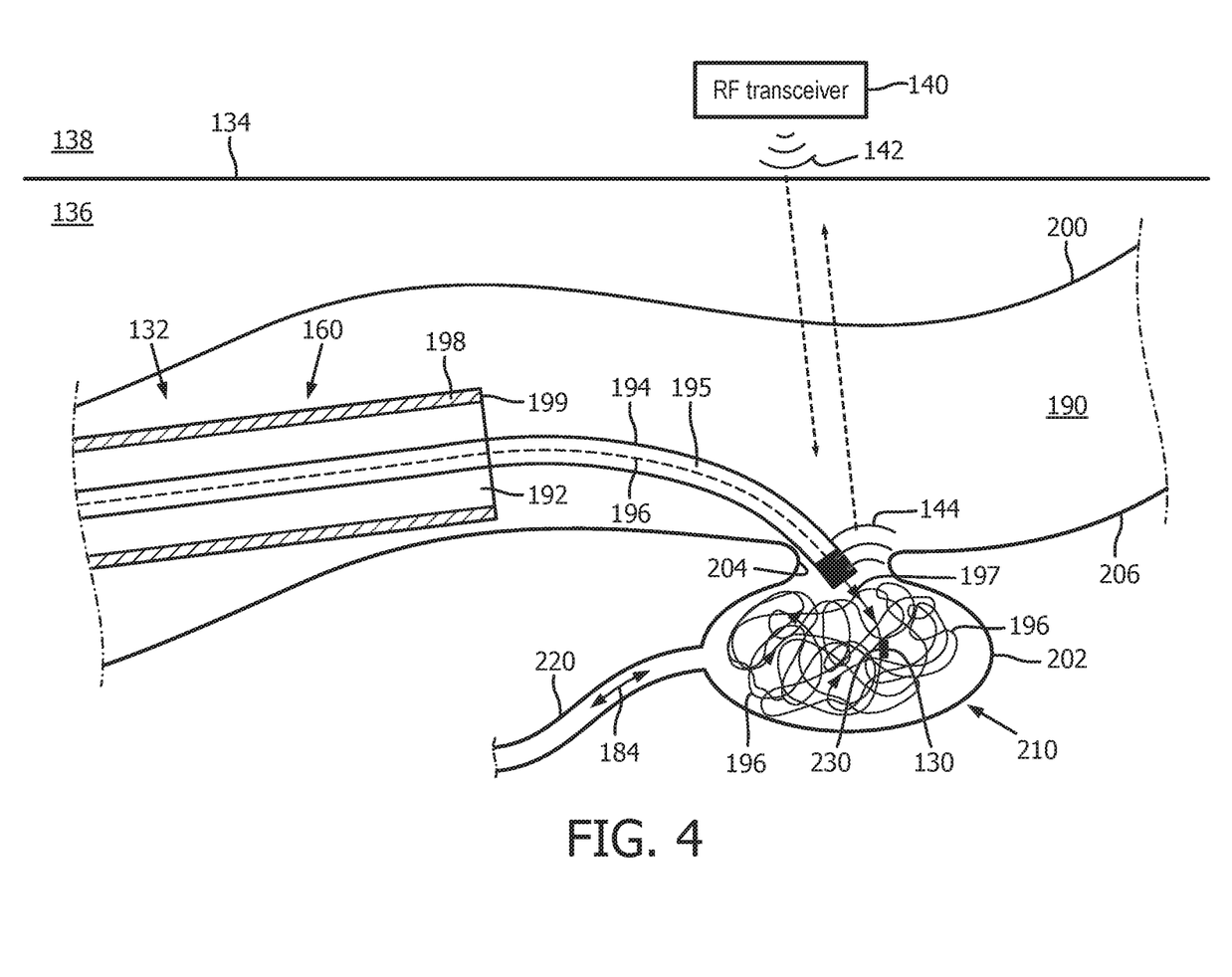
FIG. 4 is a diagrammatic, partial cross-sectional view of the catheterization instrument delivering a wire segment through the micro-catheter into the aneurysm to form a coil in the aneurysm.

Referring to FIG. 4, once the distal tip 104 of the micro-catheter 194 and the flow sensing element 130 is installed in the aneurysm 202, the flow sensing element/structure assembly 238 can be installed in the aneurysm 202. A wire segment 196 can be passed through the lumen 195 of the micro-catheter 194 to enter the aneurysm 202 and begin forming a coil 210. As stated above, the wire segment 196 can also be the structure 230 and carry the flow sensing element 130 into the aneurysm 202. However, the assembly 238 can be installed in the aneurysm 202 using additional structures 230 prior to installing the wire segment 196 and forming the coil 210. The RF transducer 130 can continue to supply fluid flow measurements to the RF transceiver 140 while coils 210 are being formed (or placed) in the aneurysm 202.

A fibrous material 197 can be attached along the wire segment 196 for enhancing clotting of blood around and in the coil 210. Generally, wire segments 196 are prepared with a predetermined length before being passed through the micro-catheter 194. However, it is not a requirement that the wire segments 196 be formed to a predetermined length prior to entering the micro-catheter 194. An end of a wire segment 196 can enter the micro-catheter 194 prior to being trimmed to a desired length. As the wire segment 196 is fed through the micro-catheter 194, the wire segment 196 can be severed at a proximal end of the guide catheter 198 to produce a desired wire segment length, where the desired wire segment length can be the length at which a desired coil 210 size is produced based on the desired wire segment length.

As the coil(s) 210 are formed in the aneurysm 202, the flow sensing element 130 can transmit fluid flow measurements of fluid flowing into the aneurysm 202 from the internal flow passage 190 of the vessel 200. As one or more coils 210 are formed in the aneurysm 202, the fluid flow 182 entering the aneurysm 202 can be reduced as a result of the flow restriction provided by the coil(s). Real-time monitoring of fluid flowing into the aneurysm 202 from the vessel 200 can help increase the effectiveness of the endovascular aneurysm coiling procedure. Current procedures make calculated estimates as to the number of coils that are needed to prevent fluid flow into the aneurysm 202. This can possibly be a reason that many coiling procedures are not successful in treating the aneurysm 202. Without real-time monitoring of the parameter (i.e. fluid flow into the aneurysm) which can determine success or failure of the procedure, then termination of the procedure prior to its successful completion can result.

The current disclosure describes embodiments that provide real-time monitoring of fluid flow into the aneurysm 202. The flow sensing element 130 can be configured to detect fluid flow in the aneurysm 202 while the coiling procedure is being performed and send that detected data through the instrument 102 to the computer 122. The computer 122 can compare the detected data with expected or desired data (such as minimal or zero fluid flow) and provide appropriate indications to a display 126, which can display a graphical representation (or visual indication) of the detected data to the user. The expected or desired data can be referred to as an acceptable level of flow (182+184) into the aneurysm 202. If the coiling procedure results in the flow sensing element 130 detecting that the flow (182+184) is at or below the acceptable level, then the computer can display, via the display 126, a graphical representation to the user that an acceptable level has been achieved by the coiling procedure and the procedure can be terminated due to the indication.

If the data received from the flow sensing element 130 by the computer 122, via the RF transceiver 140, is above the acceptable level (i.e. an unacceptable flow level), then additional coils 210 can be formed in the aneurysm 202 to further restrict fluid flow into the aneurysm 202. If the additional coils 210 are successful in restricting fluid flow into the aneurysm 202 at or below the acceptable level, then the procedure can possibly be terminated, depending upon the user's interpretation of the success of the procedure, which can be based at least partially on the real-time flow data provided by the flow sensing element 130 that can remain positioned in the aneurysm 202 throughout the procedure as well as after completion of the procedure. Real-time feedback of the fluid flow parameter in the aneurysm 202 can give the user more confidence in the effectiveness of the coiling procedure and can help eliminate additional procedures on the patient in the future related to the aneurysm 202.

Additionally, since the flow sensing element 130 remains in the aneurysm 202 along with the coils, continued monitoring of the fluid flow entering the aneurysm 202 can be performed even after the patient leaves the operating room. The fluid flow entering the aneurysm 202 can be monitored via the RF transducer 130, the RF transceiver 140, and the computer 122, while the patient is in recovery at the hospital or clinic, as well as when the patient is home recovering, and much later after the patient has recovered from the procedure and follow-up visits with a physician occur to verify the lasting success of procedure.

Another benefit of the real-time monitoring of fluid flow entering the aneurysm 202 can be to identify possible other fluid sources that may also be contributing fluid flow into the aneurysm 202 other than the fluid flow 182 from the vessel 200. If the coiling procedure is continued for a period of time without achieving at or below an acceptable level of fluid flow in the aneurysm 202, then the user may determine that one or more additional sources of fluid flow can be contributing to the level of fluid flow in the aneurysm 202. Without the real-time monitoring provided by the flow sensing element 130 positioned within the aneurysm 202, the coiling procedure might have been terminated before reducing level of fluid flow in the aneurysm 202 to at or below the acceptable level. With the real-time monitoring, the user can have visibility into whether or not the coiling procedure is successful in limiting the level of fluid flow in the aneurysm 202 to at or below the acceptable level. If not yet successful, then the coiling procedure can continue by adding additional coils into the aneurysm 202. If it is determined that a secondary source 220, such as vessel, is also supplying fluid flow 184 into the aneurysm 202, then other diagnostic procedures can be performed (such as imaging) to detect and determine the location of the secondary source 220 and/or additional sources.

When the location and the characteristics of the secondary source 220 are determined, then steps can be taken to shut-off or at least further restrict the fluid flow 184 into the aneurysm 202. If the fluid flow 184 originates from another vessel (not shown) that can be accessed by an additional coiling apparatus (such as another micro-catheter 194), then additional coils can be placed in the secondary source 220 to restrict flow through the secondary source 220 into the aneurysm 202. Of course, other procedures may be needed to reduce the fluid flow (182+184) into the aneurysm 202. It should be noted, that the need for an additional procedures may not be apparent without the use of real-time monitoring provided by the systems and methods of the current disclosure.

Figure 5:
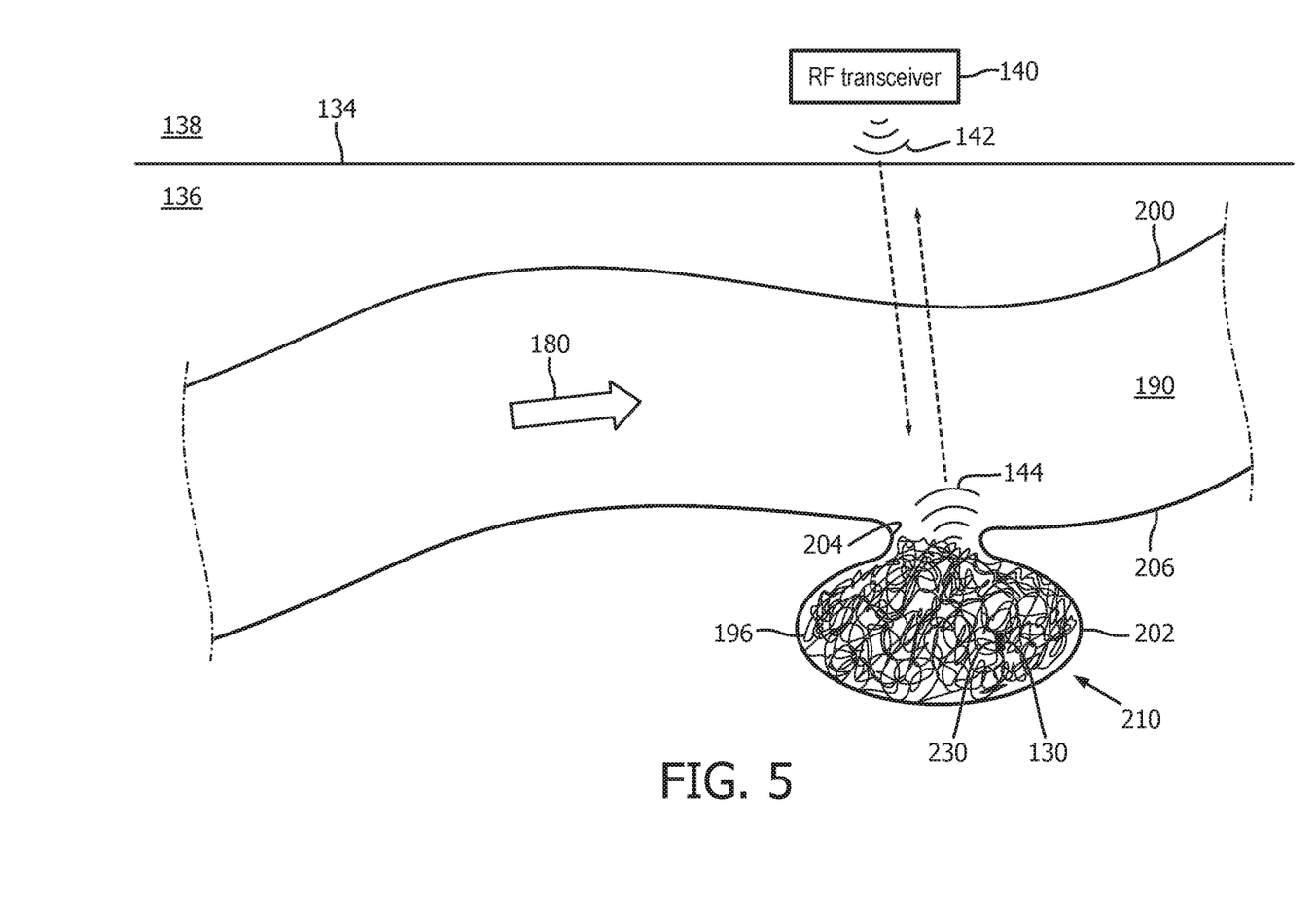
FIG. 5 is a diagrammatic, partial cross-sectional view of the completed coiling procedure with the catheterization instrument removed, and the aneurysm filled with the coil(s) and the flow sensing element left in the aneurysm.

Referring to FIG. 5, the aneurysm 202 is shown filled with coil(s) 210. Once the user determines that the level of fluid flow in the aneurysm 202 is at or below the acceptable level, then the guide catheter 198 and micro-catheter 194 can be removed from the vasculature leaving the coil(s) 210 and the flow sensing element 130 in place in the aneurysm 202. The fluid, such as blood, will clot around and in the coil(s) which can help to further ensure that fluid flow into the aneurysm 202 will not cause additional health issues for the patient. FIG. 5 also illustrates, as mentioned above, how the flow sensing element 130 (or RF transducer 130) can continue to provide fluid flow measurements to the computer 122 via the RF transceiver 140, by remotely sensing the electromagnetic signals 144 generated by the flow sensing element 130 to represent flow measurements of fluid in the aneurysm 202.

Figure 6:
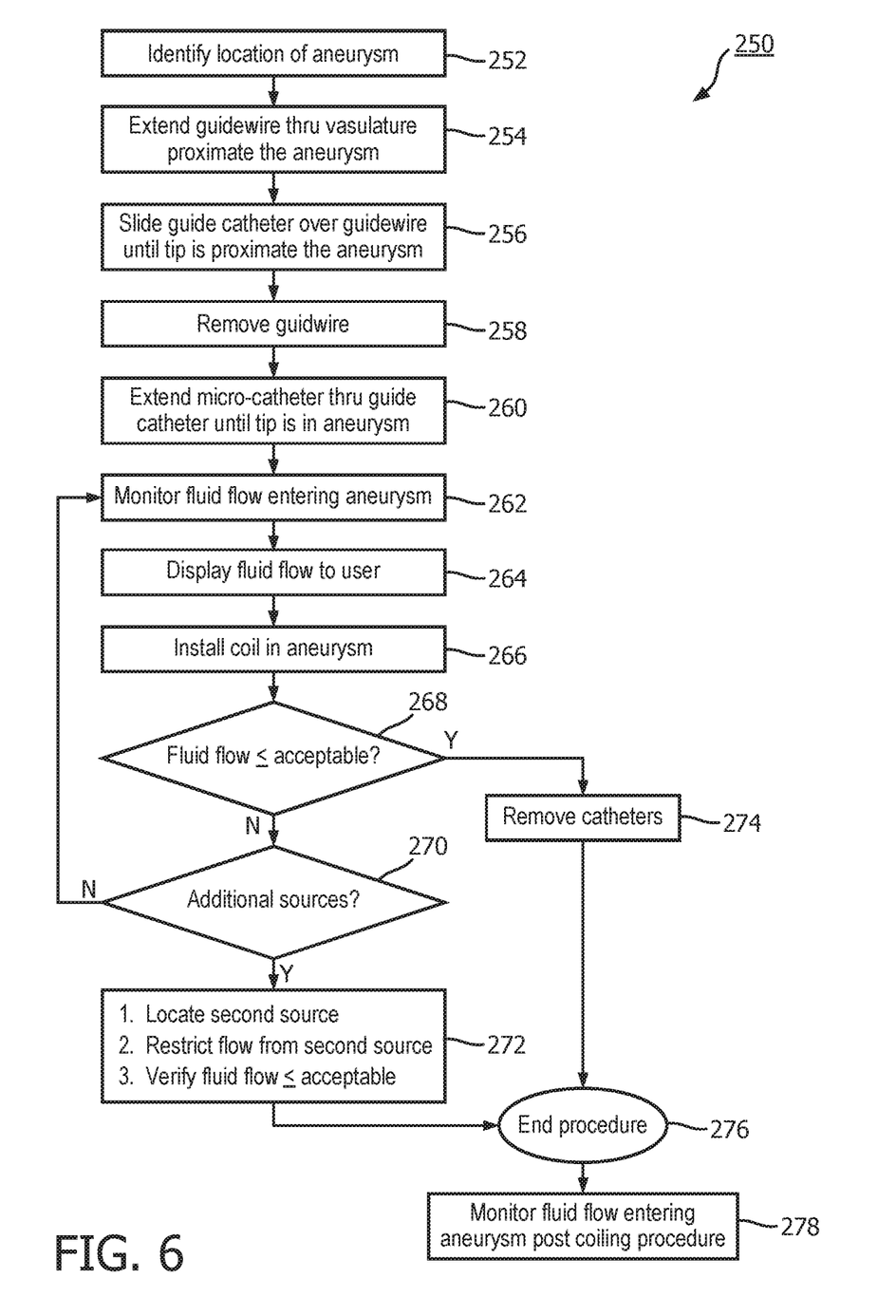
FIG. 6 is a flow chart illustrating operations for monitoring the effectiveness of an endovascular aneurysm coiling procedure.

Referring to FIG. 6, a representative flow chart of method 250 is provided. Method 250 can be used to evaluate the effectiveness of an endovascular aneurysm coiling procedure. Operation 252 includes identifying an aneurysm 202 in a patient's vasculature. This operation can be performed by various well-known procedures, which will not be discussed in detail in this disclosure. Once the aneurysm 202 has been found and a path through the vasculature identified, then a guidewire can be extended along the identified path in operation 254 to position the distal tip of the guidewire (not shown in the figures) proximate the aneurysm 202. In operation 256, a guide catheter 198 can be slid over the guidewire to guide the guide catheter 198 such that the distal end 199 of the guide catheter is positioned in the vessel 200 proximate the aneurysm 202. Then, in operation 258, the guidewire can be removed from the guide catheter 198, thus opening up the lumen 192 in the guide catheter 198 to allow insertion of other treatment devices. In operation 260, a micro-catheter 194 can be extended into the guide catheter 198, such that the distal tip 104 of the micro-catheter 194 is extended past the distal end 199 of the guide catheter 198 and into the aneurysm 202 through the opening 204 in the wall 206 of the vessel 200.

The micro-catheter 194 can deliver a flow sensing element 130 (such as an RF transducer 130) into the aneurysm 202, as described in more detail above regarding FIG. 3. With the flow sensing element 130 positioned in the aneurysm 202, the fluid flow entering the aneurysm 202 can be monitored in operation 262 via the electromagnetic signals 144 generated by the RF transducer 130. A graphical representation of the fluid flow measurements of the flow sensing element 130 can be displayed on a display 126 by the computer 122, such that the graphical representation indicates the fluid flow in the aneurysm 202, as well as whether or not the fluid flow is at or below an acceptable level. If the fluid flow is indicated as being above the acceptable level (or being at an unacceptable level), the user can install one or more coils 210 in the aneurysm 202. Since the flow sensing element 130 is monitoring the fluid flow in the aneurysm 202 in real-time (or at least very near real-time, such as less than a second for the display 126 to update with new measurement values), the user can view the graphical representation on the display 126 to determine whether or not the fluid flow is acceptable in operation 268. If the fluid flow is at or below an acceptable level, then the catheters 194, 198 (guide and micro) can be removed in operation 274, and the procedure can be complete as indicated in operation 276.

However, if in operation 268, the fluid flow level in the aneurysm 202 is at an unacceptable level, then the method can proceed to operation 270 to determine if additional sources are providing fluid flow into the aneurysm 202. If additional sources are not identified or indicated, then operations 262, 264, 266, 268 and 270 can be repeated until the fluid flow is at or below an acceptable level, which would result in the catheters being removed and the procedure ending. These operations 262, 264, 266, 268 and 270 can be repeated until an additional source is indicated or identified in operation 270. If is determined that an additional source is supplying fluid to the aneurysm 202, the method 250 can proceed to operation 272, where the additional source (or secondary source 220) is located, a procedure is performed to restrict fluid flow from the secondary source 220 into the aneurysm 202, and the fluid flow in the aneurysm 202 is verified to be at or below an acceptable level. Then the procedure can end in operation 276. If the fluid flow is not at an acceptable level, then other procedures may need to be performed to identify additional contributors to the fluid flow in the aneurysm 202 that may be outside the scope of this method. It should be noted that during this method, the flow sensing element 130 continues to update in real-time the fluid flow entering the aneurysm 202 which provides much needed feedback as to the effectiveness of the coiling procedure. After the procedure has ended in operation 276, the method 250 can proceed to operation 278, where monitoring of the fluid flow in the aneurysm 202 can continue even after the coiling procedure has ended.

The method 250 can include additional operations, omit operations, reorder the operations, and/or otherwise be modified without departing from the scope of the present disclosure.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system comprising:
   a structure configured to pass through a vasculature;
   a wire segment configured to form a coil in an aneurysm, wherein, the wire segment has a first state that does not comprise a coil when the wire segment is disposed outside of the aneurysm and a second state once a portion of the wire segment is disposed inside of the aneurysm and forms a coil in the aneurysm;
   a flow sensing element supported by the structure;
   a flexible elongate member detachably attached to the structure, wherein the structure comprises a detached state when positioned in the aneurysm and retains the flow sensing element within the aneurysm; and
   a computer in communication with the flow sensing element, the computer configured to:
   detect, at the computer and after positioning the structure within the aneurysm in the vasculature, a measurement of fluid flow entering the aneurysm based on data obtained by the flow sensing element; and
   provide a visual indication to a user as to whether the fluid flow measurement is at an unacceptable fluid flow level.

2. The system of claim 1, further comprising a first flexible elongate member having a proximal portion, a distal portion, a central longitudinal axis, and a lumen extending along the central longitudinal axis, the first flexible elongate member sized and shaped for insertion into the vasculature.

3. The system of claim 2, wherein the flow sensing element is a radio frequency transducer (RF) transducer that detects fluid flow entering the aneurysm.

4. The system of claim 3, wherein the RF transducer communicates wirelessly with an RF transceiver.

5. The system of claim 4, wherein the computer is further configured to interrogate the RF transducer, via the RF transceiver, and receive data from the RF transducer, via the RF transceiver, with the data being representative of fluid flow entering the aneurysm.

6. The system of claim 4, wherein the computer is further configured to interrogate the RF transducer, via the RF transceiver, after the first flexible elongate member is removed from the vasculature and receive data from the RF transducer, via the RF transceiver, after the first flexible elongate member is removed.

7. The system of claim 2, wherein the wire segment is configured to pass through the lumen, wherein the wire segment forms the coil in the aneurysm as the wire segment is passed through the lumen, and wherein the aneurysm is in a wall of a vessel in the vasculature.

8. The system of claim 7, wherein the structure is selected from a group consisting of the wire segment, a substrate, a container, and a flexible material.

9. The system of claim 8, wherein the structure can be delivered to the aneurysm via a second flexible elongate member and deposited in the aneurysm by a detachable connector that releasably connects the structure to a distal end of the second flexible elongate member, and wherein the structure and the flow sensing element remain in the aneurysm when the first and second flexible elongate members are removed from the vasculature.

10. The system of claim 7, wherein the computer is further configured to detect, at the computer and after forming the coil in the aneurysm, the measurement of fluid flow entering the aneurysm.

11. The system of claim 7, wherein the wire segment includes fibrous material fixedly attached along the wire segment, and wherein the fibrous material enhances clotting in and around the coil.

12. The system of claim 7, wherein the wire segment comprises multiple wire segments, and each one of the wire segments forms a coil when the respective wire segment passes through the lumen and into the aneurysm.

13. The system of claim 1, wherein the computer is further configured to:
  determine, at the computer, that the fluid flow measurement is at or below an acceptable fluid flow level; and
  provide a visual indication to a user as to whether the fluid flow measurement is at or below the acceptable fluid flow level.

14. A method of evaluating an endovascular aneurysm coiling procedure, the method comprising:
  guiding a distal portion of a first flexible elongate member through a vasculature and into an aneurysm in a vessel of the vasculature;
  delivering a flow sensing element to the aneurysm by guiding the flow sensing element through a lumen that extends through the first flexible elongate member, wherein the delivering further comprises passing a second flexible elongate member through the lumen, and depositing the flow sensing element in the aneurysm by releasing a detachable connector that releasably connects a structure, on which the flow sensing element is disposed, to a distal end of the second flexible elongate member;
  detecting, at a computer and after positioning a coil within the aneurysm, a first measurement of fluid flow entering the aneurysm based on data obtained by the flow sensing element disposed in the aneurysm, with the flow sensing element in communication with the computer;
  determining, at the computer, that the first fluid flow measurement is at or below an acceptable fluid flow level; and
  outputting, to a display in communication with the computer, a first graphical representation that the first fluid flow measurement is at or below the acceptable fluid flow level.

15. The method of claim 14, further positioning a further coil when the first fluid flow measurement is at an unacceptable level, wherein the positioning the further coil, detecting the first fluid flow measurement, the determining, and the outputting are repeated until the first fluid flow measurement is at or below the acceptable level.

16. The method of claim 14, further comprising passing a wire segment through a first flexible elongate member such that the wire segment exits from a distal portion of the first flexible elongate member and gathers together in the aneurysm to form the coil in the aneurysm, thereby positioning the coil within the aneurysm.

17. The method of claim 14, wherein the structure is selected from the group consisting of a wire segment, a substrate, a container, and a flexible material.

18. The method of claim 14, further comprising:
  removing the first and second flexible elongate members from the vasculature, wherein the structure remains in the aneurysm after the removing; and
  detecting, at the computer and after the removing, a second measurement of fluid flow entering the aneurysm based on data obtained by the flow sensing element.

19. A system comprising:
  a catheter configured to pass through a vasculature and having a lumen through which a wire segment passes, the catheter configured to perform an endovascular aneurysm coiling procedure in which the wire segment is pushed into an aneurysm of the vasculature and forms a blood flow-blocking coil within the aneurysm;
  a flow sensing element disposed on a structure such that the flow sensing element can be pushed into the aneurysm via the catheter and is disposed in proximity to the blood flow-blocking coil formed within the aneurysm in the endovascular aneurysm coiling procedure;
  a flexible elongate member attachable to the structure with a detachable connector, the flexible elongate member configured for delivering the flow sensing element to the aneurysm by guiding the structure through a lumen that extends through the catheter; and
  a computer in communication with the flow sensing element, the computer configured to detect, at the computer and after the flow sensing element is pushed into the aneurysm with the wire segment and after formation of the blood flow-blocking coil, a measurement of fluid flow entering the aneurysm based on data obtained by the flow sensing element.

20. A system according to claim 19 in which the structure comprises the wire segment.

* * * * *